(12) United States Patent
Mahootchi

(10) Patent No.: US 10,292,998 B1
(45) Date of Patent: May 21, 2019

(54) COMPOSITIONS AND METHODS FOR PREVENTION AND TREATMENT OF EYE INFECTIONS

(71) Applicant: Ahad Mahootchi, Tampa, FL (US)

(72) Inventor: Ahad Mahootchi, Tampa, FL (US)

( * ) Notice: Subject to any disclaimer, the term of this patent is extended or adjusted under 35 U.S.C. 154(b) by 0 days.

(21) Appl. No.: 16/056,852

(22) Filed: Aug. 7, 2018

(51) Int. Cl.
- *A61K 9/00* (2006.01)
- *A61K 31/79* (2006.01)
- *A61P 27/02* (2006.01)
- *A61P 31/02* (2006.01)
- *A61K 31/198* (2006.01)

(52) U.S. Cl.
CPC ............ *A61K 31/79* (2013.01); *A61K 9/0048* (2013.01); *A61K 31/198* (2013.01); *A61P 27/02* (2018.01); *A61P 31/02* (2018.01)

(58) Field of Classification Search
None
See application file for complete search history.

(56) References Cited

U.S. PATENT DOCUMENTS

| | | |
|---|---|---|
| 2009/0170932 A1 | 7/2009 | Aggarwal et al. |
| 2013/0171239 A1 | 7/2013 | Gilbard |
| 2014/0322345 A1 | 10/2014 | Liang et al. |
| 2016/0045536 A1 | 2/2016 | Samson et al. |
| 2016/0199225 A1 | 7/2016 | Ivri |

FOREIGN PATENT DOCUMENTS

| | | |
|---|---|---|
| EP | 0848951 A1 | 6/1998 |

OTHER PUBLICATIONS

A.B. Epstein & C.J. Quinn. "Diseases of the Conjunctiva." Ch. 25 (pp. 437-482) of J.D. Bartlett & S.D. Jaanus, Clinical Ocular Pharmacology, 5th Edition, Elsevier Health Sciences (2008).

*Primary Examiner* — Brian J Davis
(74) *Attorney, Agent, or Firm* — Rosenberg, Klein & Lee

(57) ABSTRACT

A low-irritation medication for treatment and prevention of eye infections is provided by a preparing a composition of povidone-iodine (PVP-I), N-acetylcysteine (NAC), and an aqueous solution. The composition is then applied to the eye of a patient. The composition is shown to be effective at resolving viral conjunctivitis within 48 hours even at lower concentrations. The composition is also shown to be effective at treating other eye infections, and at reducing causes of infectious to prevent antisepsis during surgery. The composition may be as much as 80% PVP-I by volume without requiring anesthetic to reduce irritation to tolerable levels upon application to the eyeball, and both 10% PVP-I, 1% NAC and 5% PVP-I, 0.5% N NAC compositions are shown to be less irritating than a 1.25% PVP-I composition without NAC.

20 Claims, No Drawings

COMPOSITIONS AND METHODS FOR PREVENTION AND TREATMENT OF EYE INFECTIONS

FIELD OF THE INVENTION

The field of the invention is directed to medical compositions and methods of preparing the medical compositions for use in medical procedures.

Additionally, the field of the subject composition and method is related to the field of ophthalmic treatment procedures, and to preparing treatment compositions for ophthalmic procedures and conditions.

Furthermore, the field of the subject composition and method is generally directed to treatment and prevention (e.g. prophylaxis) of eye infections experienced by a patient.

More particularly, the subject composition and method is in the field of treating and preventing eye infections caused by viruses, bacteria, parasites, and fungi which are capable of attacking the surface or the interior of a patient's eyes.

Furthermore, the subject composition and method is directed to the field of treating patients affected by afflictions of the conjunctiva and cornea, which are the membranes of the inner eyelid and the eye's surface. The subject composition and method are also directed at preventing infection on or in the eye during or after surgical procedures.

More particularly, the subject composition and method is directed to compositions and methods for treating patients afflicted with conjunctivitis causing inflammation of the eyelid (blepharitis), the cornea (keratitis), the vitreous humour (vitritis), the retina and blood vessels associated with the eye (chorioretinitis) and the optic nerve; and preventing surgically related infections of the lid, conjunctiva, cornea, anterior chamber and vitreous, retinas and optic nerve of the eye.

BACKGROUND OF THE INVENTION

Eye infections have long been a major health problem concern and may be caused by viruses, bacteria, parasites, and fungi which are capable of attacking the surface or the interior of a patient's eye. Infections may more particularly occur as a complication after surgery, which can be particularly devastating for the patient, whether human or animal.

A common form of eye infection experienced by patients is an inflammation of the conjunctiva, which are the membranes of the inner eyelid and the inner corner of the eye's surface. In general, this type of infection is termed "conjunctivitis," and is commonly referred to as "pink eye." The inflammation may more specifically affect the eyelid (termed blepharitis) or the cornea (keratitis), among other portions of the eye and surrounding tissue. Conjunctivitis has multiple infectious causes, including bacteria, viruses, and fungi. Non-infectious irritants to the eye, including allergies, foreign bodies entering the eye, and chemical exposure, may also generate the same symptoms.

Conjunctivitis may result in itchiness and pain in one or both eyes, along with a redness or pinkness, and produces an increase in discharges such as tears and pus from the region of the eyeball. These symptoms combine to make the infectious causes of conjunctivitis highly contagious if proper hygiene is not observed, as the infected patient tends to rub their eyes frequently, transferring the discharges—and any infectious agent present—to their hands. The infectious agent can then be spread through direct contact with an infected individual, or exposure to contaminated surfaces touched by the infected individual. The infectious agent may also be transferred to other portions of the patient's body, causing secondary infections to organs and internal tissues. Since newborns habitually contact both their own face and nearby objects, neonatal conjunctivitis is a common concern.

Bacterial conjunctivitis is caused by bacteria which infect the eye through a number of sources of contamination. The most common types of bacteria which cause bacterial conjunctivitis include *staphylococcus aureus, haemophilus influenza, streptococcus pneumoniae,* and *pseudomonas aeruginosa*. Gonorrhea and *chlamydia* may also trigger bacterial conjunctivitis as a complication. Symptoms of the bacterial conjunctivitis generally include a thick eye discharge or pus. Antibiotics have been used to eliminate the bacteria; they are generally applied with topical and antibiotic eye drops or eye ointments.

Viral conjunctivitis is caused by a virus, frequently an adenovirus. Viral conjunctivitis generally produces a watery discharge. Antibiotics are generally not effective against viruses, although they may be used to prevent secondary infections. The common approach to viral conjunctivitis is to treat the symptoms and otherwise let the disease run its course, typically over one or two weeks. This approach is not ideal, due both to the contagious nature of viral conjunctivitis and the present risk of complications; however, past attempts to treat the underlying cause have met with no success in many cases. The field of medicine has generally focused on prevention through methods such as hygiene.

In a related field, surgical prophylaxis is the sterilization of the ocular surface and regions around the eye prior to surgery. Since pathogens and normal ocular flora may enter surgical wounds or infect ocular surface tissues after surgical procedures, surgical prophylaxis is critical to avoiding non-optimal surgical outcomes. However, due to the sensitivity of the eye tissues, a very limited number of sterilizing agents are available that are not intolerable or downright harmful when applied to the eyeball.

PRIOR ART

Povidone-iodine (PVP-I), sometimes referred to as iodopovidone or by its common brand name of Betadine®, has been used as a disinfectant to reduce bacterial colony counts. Sufficient concentrations of PVP-I has also been used against adenoviral infections, such as adenoviral keratoconjunctivitis, and other external ocular infections; in such cases, a drop of 5%-10% PVP-I by volume is applied, for example from a syringe, into the eye. However, PVP-I applied to the human eye, especially at concentrations greater than 2.5% by volume, has been found to cause extreme immediate pain and a continuing burning sensation. Tolerance for pain varies from one individual to another and is thus not a quantitative parameter which can be realized. However, the use of PVP-I as a disinfectant for the eye of a patient is greatly hampered by the general effect this composition has on the nerve system of patients undergoing ophthalmic procedures.

N-acetylcysteine (NAC), which is sold under various brand names including Mucomyst®, is a non-inflammatory composition used in a number of medical procedures. Although widely used as an aid in reducing inflammation, it is not believed that the desensitization of a patient's eye is accomplished through the sole use of NAC.

It is believed that the preparation of a composition combining NAC with PVP-I in predetermined amounts for ophthalmic procedures has not been attempted.

Thus, there is a long-standing need for the application of a treatment composition which will effectively serve as a disinfectant to reduce the bacterial colony counts in a patient's eye undergoing an ophthalmic procedure, while simultaneously relieving the pain of the PVP-I experienced by the patient.

SUMMARY OF THE INVENTION

It is an object of the disclosed composition and method to improve the treatment of eye infections in patients undergoing ophthalmic procedures.

It is another object of the disclosed composition and method to provide a medication which is more effective than existing povidone-iodine (PVP-I) solutions in the treatment and prevention of eye infections.

It is a further object of the disclosed composition and method to provide a medication which is more tolerable, in terms of irritation and discomfort, than existing povidone-iodine (PVP-I) solutions in the treatment and prevention of eye infections.

It is yet another object of the disclosed composition and method to provide a treatment composition which is more effective than prior art treatments in the treatment of conjunctivitis.

It is still another object of the disclosed composition and method of providing a treatment composition which is effective in treating viral conjunctivitis.

It is a further object of the disclosed composition and method to provide for improved methods of treating eye infections by providing a predetermined amount of povidone-iodine (PVP-I) in combination with a predetermined amount of N-acetylcysteine (NAC) and blending the PVP-I with the NAC in predetermined amounts into an aqueous solution forming a treatment composition.

It is yet another object of the disclosed composition and method to apply the treatment composition to the patient's eye to reduce bacterial count through the combination while simultaneously relieving the patient of any pain associated with PVP-I treatment.

In overall concept, the subject composition and method is directed to a treatment and/or prevention of eye infections where a predetermined amount of PVP-I is established and then blended with a predetermined amount of NAC into an aqueous solution to form a treatment composition. The treatment composition is then applied to a patient's eye to treat an eye infection, or to disinfect the eye prior to a surgical procedure to prevent infection during the surgical procedure (surgical prophylaxis).

In certain embodiments of the subject composition and method, the PVP-I is within the range of 1.0%-80% of the overall treatment composition volume. In certain embodiments, the predetermined amount of NAC is within the range of 0.5%-10% of the overall treatment composition volume.

As a preferred embodiment, the PVP-I is within the range of 1.25%-2.5% of the overall treatment composition volume, with the NAC being within the range of 0.5%-1.0% of the overall treatment composition volume. In another preferred embodiment, the PVP-I is within the range of 10%-80% of the overall treatment composition volume, with the NAC being within the range of 2.0%-10% of the overall treatment composition volume.

In the embodiments as described herein, the predetermined amount of the aqueous solution within which the PVP-I and NAC are incorporated is within the range of 10.0%-98.7% by volume of the overall treatment composition. In various embodiments, the aqueous solution is water or a saline solution.

In accordance with the composition and method as herein described, the treatment composition is applied with at least 7.0 microliters of the treatment composition to the patient's eye. At least one drop of the treatment composition is applied by a syringe or other method into the eye of the patient. In a preferred embodiment, the treatment composition is applied at least twice to the eye over a predetermined time interval within the range of 30-180 seconds.

In other embodiments, a steroid such as prednisolone is incorporated into the treatment composition prior to the application of the treatment composition to the eye of the patient.

These and other objects may be attained to provide a low-irritation medication for treatment and prevention of eye infections.

Additional aspects, details, and advantages of the disclosed system and method will be set forth, in part, in the Description of the Preferred Embodiments which follows.

DETAILED DESCRIPTION OF THE PREFERRED EMBODIMENTS

Reference will now be made in detail to exemplary embodiments. The embodiments are described below in order to explain the disclosed composition and method.

Povidone-iodine (PVP-I) is an antiseptic broadly used in the field of medicine, effective at blocking the spread of bacteria, viruses, and fungi. PVP-I is also effective as an antibacterial agent to prevent antisepsis during eye surgery. One pre-treatment approach is to drip a 0.5%-0.7% PVP-I solution, by volume, into the eye over 30 seconds and allow the solution to rinse out naturally, the process being repeated every 90 seconds four times. This has been shown to result in a reduction of 99.9% of bacteria on the eye surface. However, PVP-I has been shown to be largely ineffective at treating pre-existing infections, especially viral infections such as viral conjunctivitis.

Another disadvantage of existing PVP-I solutions is that they are unpleasantly painful and often intolerable when applied to the surface of the eye, with residual discomfort remaining for hours or even days. At even 10% concentration by volume, the pain has been found to be intolerable during application. PVP-I is therefore generally provided at 1.25% or 2.5% concentrations, at which it has been found in some cases to be tolerable but still highly irritating; however, lower concentrations of PVP-I result in a less effective treatment composition in the reduction of bacteria count and/or preventing infection.

Irritation resulting from the use of PVP-I can be further reduced by using various local anesthetics. However, medical personnel are hesitant to provide anesthetic when the pain is not intolerable, due to the risk of addiction or abuse. In general, the patient is in most circumstances asked to tolerate the discomfort (for, as noted, several hours), and is only provided an anesthetic when PVP-I concentrations of 5% or higher are applied.

Experiments have determined that PVP-I can be mixed with N-acetylcysteine (NAC), preferably in combination with an aqueous solution such as saline or water for improved lubrication, to form a medical eye drop treatment, which has the unexpected result of greatly reducing the bacteria count while simultaneously maintaining the pain at a tolerable level, or in some cases reducing the pain to a non-perceptible level. The active treatment components are preferably mixed by stirring at room temperature (that is, roughly 15-25° C.) and added to an aqueous solution. The PVP-I concentration of the mixture can be as low as 1.25% by volume of the treatment composition without substantially reducing its effectiveness at preventing eye infections of bacterial, viral, and fungal varieties. Additionally, the mixture has proven effective at combatting at least some forms of pre-existing infection, in contrast to a PVP-I solution which does not include NAC.

Experiments were performed with differing ratios of PVP-I, NAC, and aqueous solution in combination. The PVP-I percentage by volume was varied between 0.5% and 80%, and the NAC percentage by volume was varied between 0.5% and 10%. The combinations were then applied, with one or more drops of the composition, each between 7 and 30 microliters in total volume, applied by syringe to the eye of a patient over a period of between 30 and 180 seconds.

It was found that, even at a lower range of PVP-I between 1.25% and 2.5%, bacterial count on the surface of the eyeball was acceptably reduced, showing improvement over similar experiments where PVP-I alone was used at the same percentages. In comparison, experiments using NAC alone was ineffective in lowering bacterial count.

Additional experiments were performed with the same combinations in treating a viral infection, with similarly effective results. In one experiment, a mixture comprising 1.25% PVP-I and 10% NAC by volume was applied to the eyeball of human patients suffering from viral conjunctivitis. A viral DNA test, namely the AdenoPlus® test provided by Rapid Pathogen Screening®, was conducted to confirm an adenovirus infection before treatment began. A second test consistently found no trace of viral conjunctivitis 48 hours later, as compared to the normal infection time of one to two weeks. In contrast, a previous study employing a solution of 1.25% PVP-I by volume without NAC showed no significant effect on viral conjunctivitis infections. (See *Clinical Ocular Pharmacology,* 5th Edition, eds. J. D. Bartlett & S. D. Jaanus, Elsevier Health Sciences (2008), p. 454.) With the benefit of hindsight, it is theorized that the viral conjunctivitis was defended from the PVP-I treatment in the earlier study by the mucus that naturally forms with conjunctivitis, which was dissolved by the NAC.

In cases where viral conjunctivitis was not detected by the test prior to treatment but comparable symptoms were present (e.g. bacterial conjunctivitis), the described composition was still shown to resolve the symptoms completely within 72 hours. The treatment is therefore generally effective against conjunctivitis regardless of the underlying cause.

Furthermore, during the above experiments, there was found to be only minor discomfort even as the PVP-I percentage was increased beyond the usually recommended percentages. That is, a mixture of PVP-I and NAC was determined to be considerably less irritating than the same concentration of PVP-I without NAC. In one experiment, a mixture comprising 10% PVP-I and 1% NAC by volume was applied to the eyeball of human patients and reported to be less irritating than the 2.5% PVP-I concentration with no NAC. Similar results were produced with 5% PVP-I and 0.5% NAC by volume. It was further demonstrated that a mixture of 80% PVP-I and 4% NAC could be tolerated without anesthetic, producing an extremely effective antiseptic; this mixture is expected to be exceptional for surgical prophylaxis, thoroughly cleansing the eyeball of the causes of infection using levels of PVP-I which would be otherwise excruciating. Additionally, because the effect is completely localized to the surface of the eyeball, NAC has no apparent risk of addiction, and the treatment can therefore be safely used in all circumstances.

In summary, the above experiments determined that NAC without PVP-I was ineffective in treating or preventing infections; that PVP-I without NAC was effective but highly uncomfortable in treating and preventing bacterial infections, and ineffective at treating viral infections; and that the combination of PVP-I and NAC was effective at treating and preventing both bacterial and viral infections with only minor discomfort.

In certain embodiments, the medical composition also includes a steroid, such as a corticosteroid, which further relieves symptoms such as swelling, redness, itching, and inflammation. Corticosteroids are any of a group of steroid hormones produced in the adrenal cortex or formed synthetically; these steroids include glucocorticoids and mineralocorticoids. One such steroid is prednisolone, which is used to treat certain eye conditions due to inflammation or injury. Experiments have shown that adding steroids to the solution speeds the reduction of the symptoms of conjunctivitis. The steroid may be included in the aqueous solution prior to the initial blending with the PVP-I and NAC, added at the same time as the PVP-I and NAC, or added to an existing mixture of PVP-I, NAC, and aqueous solution. However, steroid treatments have certain disadvantages known in the art, such as contra-indications with other medicines and conditions, and should be included or not included based on these considerations. In particular, steroids should not be included when treating a patient with ocular herpes, as they have been shown to inflame the condition rather than treat it.

It is noted that NAC and PVP-I solutions are far less effective when applied separately, in comparison to a composition which mixes the two. An average eye drop contains 35 microliters, but the space between the human eye and the eyelid can only contain, in an average adult human, approximately 7 microliters of liquid. A human instinctively blinks upon addition of an eye drop to the eye, thereby forcing out most of the eye drop. As a result, only a fraction of a first eye drop will remain in the eye to mix with a second eye drop. Furthermore, the remainder of the first eye drop occupies the entire space and leaves no room for the second eye drop, which therefore does not mix properly with the first eye drop before being forced out completely by additional blinking. As a result, the composition described above is not achieved.

Therefore, it is preferable to first mix the NAC, PVP-I, and other substances such as prednisolone in the described proportions with saline or other inert ingredients, then apply the mixture as an eye drop to the eyeball being treated.

The descriptions above are intended to illustrate possible implementations of the disclosed system and method, and are not restrictive. While this disclosure has been made in connection with specific forms and embodiments thereof, it will be appreciated that various modifications other than those discussed above may be resorted to without departing from the spirit or scope of the disclosed system and method. Such variations, modifications, and alternatives will become apparent to the skilled artisan upon a review of the disclosure. For example, functionally equivalent elements are substitutable for those specifically shown and described, and certain features are usable independently of other features. Additionally, in various embodiments, all or some of the above embodiments are selectively combined with each other, and particular elements are reversed or interposed, all without departing from the spirit or scope of the disclosed system and method as defined in the appended claims. The scope should therefore be determined with reference to the description above and the appended claims, along with their full range of equivalents.

What is claimed is:

1. A method of treating eye infections comprising:
   (a) establishing a predetermined amount of povidone-iodine (PVP-I);
   (b) establishing a predetermined amount of N-acetylcysteine (NAC);
   (c) blending said predetermined amount of PVP-I with said predetermined amount of said NAC into a predetermined amount of an aqueous solution to form a treatment composition; and,
   (d) applying said treatment composition to a patient's eye to thereby treat an eye infection of the patient.

2. The method as recited in claim 1, wherein the predetermined amount of PVP-I is within the range of 1.0%-80% by volume of the treatment composition volume.

3. The method as recited in claim 1, wherein the predetermined amount of NAC is within the range of 0.5%-10% by volume of the treatment composition volume.

4. The method as recited in claim 1, wherein the predetermined amount of PVP-I is within the range of 1.25%-2.5% by volume of the treatment composition volume.

5. The method as recited in claim 1, wherein the predetermined amount of PVP-I is within the range of 10%-80% by volume of the treatment composition volume.

6. The method as recited in claim 1, wherein the predetermined amount of the aqueous solution is within the range of 10%-98.7% of the volume of the treatment composition.

7. The method of claim 1, wherein the blending of the predetermined amounts of PVP-I and NAC is by stirring of the PVP-I and NAC into the predetermined amount of the aqueous solution at room temperature.

8. The method of claim 1, wherein the aqueous solution is a saline solution.

9. The method of claim 1, wherein the application of the treatment composition is by applying at least 7.0 microliters of said treatment composition to the patient's eye.

10. The method of claim 1, wherein the application of the treatment composition is by applying at least one drop of said treatment composition by a syringe into the eye of the patient.

11. The method of claim 1, wherein the predetermined amount of the aqueous solution includes a steroid composition added prior to applying the treatment composition to the patient's eye.

12. The method as recited in claim 1, wherein the application of the treatment composition is by at least twice applying the treatment composition to the eye of the patient over a predetermined time interval within the range of 30-180 seconds.

13. The method as recited in claim 1, wherein the eye infection being treated is a fungal infection.

14. The method as recited in claim 1, wherein the eye infection being treated is a bacterial infection.

15. The method as recited in claim 1, wherein the eye infection being treated is a viral infection.

16. The method as recited in claim 1, wherein the eye infection being treated is viral conjunctivitis.

17. A method of preventing eye infections comprising:
   (a) establishing a predetermined amount of povidone-iodine (PVP-I);
   (b) establishing a predetermined amount of N-acetylcysteine (NAC);
   (c) blending said predetermined amount of PVP-I with said predetermined amount of said NAC into a predetermined amount of an aqueous solution to form a treatment composition; and,
   (d) applying said treatment composition to a patient's eye prior to a surgical procedure to thereby prevent eye infection of the patient during the surgical procedure.

18. The method as recited in claim 17, wherein the predetermined amount of PVP-I is within the range of 10%-80% by volume of the treatment composition volume.

19. A treatment composition for treating a patient's eye infection comprising povidone-iodine (PVP-I) blended into an N-acetylcysteine (NAC) composition and an aqueous solution for application to an eye of the patient.

20. The treatment composition as recited in claim 19, wherein the NAC is within the range of 0.5%-1.0% by volume of the treatment composition.

* * * * *